(12) United States Patent  
Yamamoto et al.

(10) Patent No.: US 7,390,390 B2  
(45) Date of Patent: Jun. 24, 2008

(54) CAPILLARY ARRAY ELECTROPHORETIC DEVICE AND AUTO SAMPLER USED FOR THE DEVICE

(75) Inventors: Shuhei Yamamoto, Hitachinaka (JP); Hiromi Yamashita, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 672 days.

(21) Appl. No.: 10/475,492

(22) PCT Filed: Apr. 25, 2001

(86) PCT No.: PCT/JP01/03573

§ 371 (c)(1),
(2), (4) Date: Apr. 27, 2004

(87) PCT Pub. No.: WO02/090968

PCT Pub. Date: Nov. 14, 2002

(65) Prior Publication Data

US 2004/0173460 A1    Sep. 9, 2004

(51) Int. Cl.
*G01N 27/453* (2006.01)
*G01N 30/84* (2006.01)
*G01N 1/20* (2006.01)

(52) U.S. Cl. .................. 204/604; 204/601; 73/863.33; 73/61.55

(58) Field of Classification Search ......... 204/451–454, 204/601–605; 73/863.32, 863.33, 864.23, 73/864.91, 23.41, 61.55, 61.68; 422/102
See application file for complete search history.

(56) References Cited

U.S. PATENT DOCUMENTS

| 5,730,850 | A | 3/1998 | Kambara et al. |
| 6,017,765 | A | 1/2000 | Yamada et al. |
| 6,203,760 | B1 | 3/2001 | van der Plaats et al. |
| 6,258,325 | B1 * | 7/2001 | Sanadi ............... 422/101 |
| 6,365,024 | B1 * | 4/2002 | Li et al. ............. 204/604 |
| 6,485,690 | B1 | 11/2002 | Pfost et al. |
| 6,495,104 | B1 * | 12/2002 | Unno et al. ......... 422/68.1 |

FOREIGN PATENT DOCUMENTS

| EP | 0 431 251 A1 | 6/1991 |
| EP | 0 864 860 A1 | 9/1998 |
| JP | 6-324054 | 11/1994 |
| JP | 9-325154 | 12/1997 |
| JP | 2001-13152 | 1/2001 |
| JP | 2001-99813 | 4/2001 |
| WO | WO-99/42819 | 8/1999 |

* cited by examiner

*Primary Examiner*—Alex Noguerola
(74) *Attorney, Agent, or Firm*—Dickstein Shapiro LLP

(57) ABSTRACT

A capillary array electrophoretic device capable of securing a sample plate array and a buffer container three dimensionally on a tray of an autosampler. A tray (700) is provided with a guide groove (701) and a stopper (702) corresponding to guides (715, 716) of sample plate assemblies (710, 711) including a microtiter plate.

13 Claims, 8 Drawing Sheets

CAPILLARY ARRAY ELECTROPHORETIC DEVICE AND AUTO SAMPLER USED FOR THE DEVICE

This application is a 371 of PCT/JP01/03573, which was filed on Apr. 25, 2001.

TECHNICAL FIELD

The present invention relates to an electrophoretic device for separating or analyzing samples such as DNA or proteins by electrophoresis using a capillary array consisting of a plurality of capillaries bundled together, and to a sampling apparatus used therefor.

BACKGROUND ART

In a well-known technique for separating or analyzing samples to be investigated, a capillary array is constructed by combining a plurality of capillaries, and then the samples to be analyzed or separated are supplied to each capillary together with an electrophoresis medium. Samples supplied to the capillaries include DNA labeled with a fluorescent substance and proteins. Such a technique is described in U.S. Pat. Nos. 5,366,608, 5,529,679, 5,516,409, 5,730,850, 5,790,729, 5,582,705, 5,439,578, and 5,274,240, for example. From the viewpoint of separation or analysis throughput, use of multiple capillaries can provide more advantages than the electrophoresis method using a slab gel.

A multicapillary array electrophoretic device includes a casing housing a constant-temperature bath for storing the capillary array in a constant temperature environment, a gel pump unit for replacing a gel polymer as a separating medium in the capillary array, an irradiation/detection unit for irradiating the capillary array with laser light or the like to detect fluorescence from fluorescence-labeled samples, and an autosampler for continuously measuring many samples, for example. An electrode is formed on one end (sample loading end) of the capillary array to which a negative voltage can be applied. When DNA is injected into the capillaries, the autosampler is moved so that the negative electrode is submerged in a solution mounted on the autosampler that contains samples, and then a voltage is applied. When electrophoresis of the injected samples is carried out, the negative electrode is submerged in a buffer solution mounted on the autosampler, and then a voltage is applied. The DNA samples and the buffer solution are mounted on a tray on the autosampler. The samples are often put in a general-purpose microtiter plate capable of storing many samples at once, which is then combined with a dedicated adapter or the like and mounted on the tray. The buffer solution is put in a buffer reservoir intended for that purpose which is mounted on the tray. The microtiter plate and the buffer reservoir are covered with septa for preventing the evaporation of the samples. The septa are provided with slits for allowing the insertion of capillaries.

The microtiter plate and the buffer reservoir are thus simply placed on the tray of the autosampler such that they are fixed in X and Y directions but not in Z direction. As a result, when the autosampler is moved downward and the sample loading end of the capillary array is removed from the wells in the microtiter plate or the buffer reservoir, the microtiter plate or the buffer reservoir could be lifted by the capillary array due to the friction between the array and the septa.

In order to prevent this, conventionally a press-down plate (to be hereafter referred to as a "stripper plate") is used. The stripper plate can be moved up and down along the sample loading end of the capillary array. For example, when a sample is introduced into the capillary array, the autosampler is initially moved in X and Y directions so as to position a target well directly below the capillary array where the sample loading end of the capillary array can be inserted into the well in the microtiter plate containing the sample. The autosampler is then moved upwards, when the stripper plate comes into contact with the autosampler and is lifted. The stripper plate exerts a force pushing the microtiter plate downward provided by a spring secured to the stripper plate or by its own weight. Thus, when the autosampler is moved downward, the microtiter plate is pressed against the tray on the autosampler until the capillary array is completely pulled out, thus preventing the lifting of the microtiter plate.

However, this technique using the stripper plate has several problems. During sample introduction or electrophoresis, for example, a downward force is exerted on the autosampler as long as the stripper plate is in contact with the autosampler. The autosampler is driven by a stepping motor, for example. Therefore, the autosampler is prevented from dropping by the static torque provided by the stepping motor as long as it is energized. When the motor is not energized, however, there is the danger of the autosampler being dropped due to the force provided by the stripper plate. For example, when the power to the device is turned off and the device is placed in a standby mode, it is necessary to keep the sample loading end of the capillary array submerged in the buffer reservoir or a water reservoir so as to prevent the drying of the capillary array attached to the device. However, as the stepping motor is not energized in this mode, the autosampler could be dropped as it is pushed by the stripper plate. A similar problem could occur when the door of the device is opened by the operator during electrophoresis or while the autosampler is moving, because opening of the door requires all the operations to be automatically stopped and various power supplies to be shut down. It is of course possible to design the device such that the autosampler would not be dropped unless it is pushed down with a force sufficiently greater than the stripper plate. This, however, would greatly inconvenience the maintenance or servicing operations where the autosampler would have to be moved manually.

Further, during sample introduction or electrophoresis, a high voltage of the order of several to several tens of kV is applied to the sample introduction end of the capillary array. As a result, there is the danger of discharge from the array electrode portion to the device chassis via the stripper plate.

These problems become increasingly pronounced as the number of capillaries in the capillary array increases, thus posing a major obstacle in increasing the throughput of the device.

Further, while the capillary array in its entirety is retained in the constant temperature bath for maintaining the array at a certain temperature, the sample loading end must be exposed outside the bath. The presence of a stripper plate makes it necessary to increase the length of the capillary portions that are outside the constant temperature bath, thereby adversely affecting the performance of electrophoresis.

It is therefore an object of the invention to provide a capillary array electrophoretic device capable of automatic operation without the use of a stripper plate.

SUMMARY OF THE INVENTION

In order to achieve the aforementioned object of the invention, a sample container such as a microtiter plate and a buffer reservoir containing a buffer solution are secured on an autosampler not only in XY plane but also in Z direction, thereby enabling automatic operation of a capillary array electrophoretic device without the use of a stripper plate.

The invention provides a capillary array electrophoretic device comprising: a capillary array made up of a plurality of capillaries with their sample injection ends arranged in order; a constant temperature bath for storing the capillary array with the sample injection ends disposed downward and exposed; and an autosampler comprising a tray on which a plurality of sample containers and buffer containers can be mounted, the autosampler being adapted to move vertically and horizontally such that, when moved upward, the sample injection ends of the capillary array exposed from the constant temperature bath can be immersed in a sample in the sample containers or a buffer in the buffer containers, wherein the autosampler further comprises means for securing the plurality of sample containers and buffer containers on the tray.

The autosampler comprises a guide and a stopper for retaining a sample plate assembly and fixing it three dimensionally on the tray, the sample plate assembly including a microtiter plate for storing samples and an adapter on which the microtiter plate is mounted.

Preferably, different types of the adapter are prepared for different microtiter plates. Preferably, the tray includes a sensor for detecting the shape of a bottom portion of the adapter in order to identify the number of wells of the microtiter plate mounted on the adapter.

The invention further provides an autosampler provided in a capillary array electrophoretic device in which a capillary array is mounted with a sample injection end exposed outside a constant temperature bath, the autosampler comprising a tray on which a plurality of sample containers and buffer containers can be mounted, the autosampler being adapted to move vertically and horizontally such that, when moved upward, the sample injection ends exposed from the constant temperature bath can be immersed in a sample in the sample containers or a buffer in the buffer containers, wherein the autosampler further comprises means for securing the plurality of sample containers and buffer containers on the tray.

BRIED DESCRIPTION OF THE DRAWINGS

FIG. 1 is a perspective view of the exterior of an electrophoretic device according to the invention, with the door to a constant temperature bath open.

FIG. 2 schematically shows the relationships among a constant temperature bath of a capillary unit, a pump unit, and so on.

FIG. 3 schematically shows the overall arrangement of the electrophoretic device of the invention.

BEST MODE FOR CARRYING OUT THE INVENTION

The invention will be hereafter described by way of examples in which a fluorescence-labeled DNA sample is used, with reference made to the attached drawings.

Figure 1:
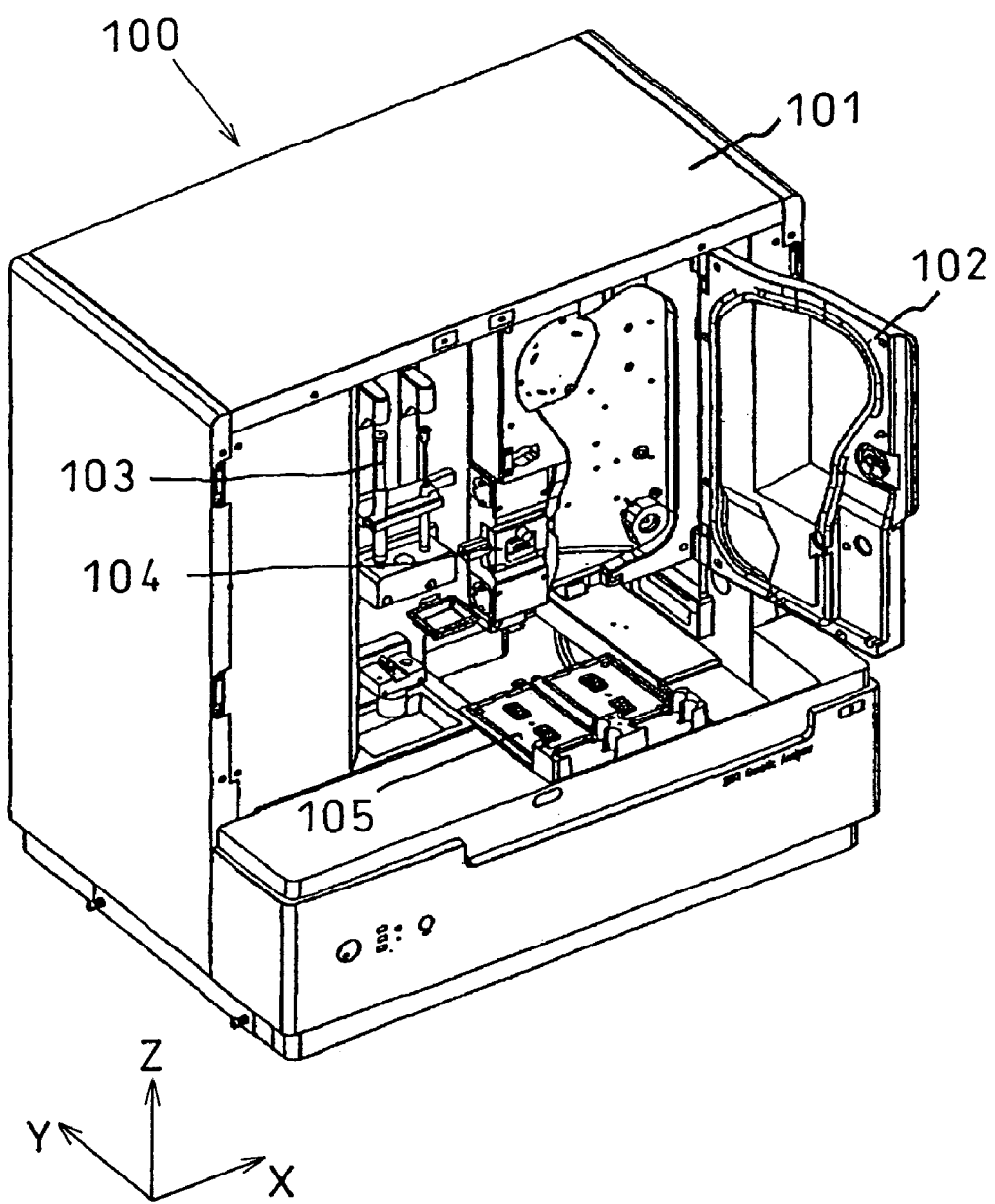

FIG. 1 shows a perspective view of the exterior of an electrophoretic device according to the invention, with the door to a constant temperature bath open. In FIG. 1, a capillary array is not yet mounted. An electrophoretic device 100 includes a chassis 101 that houses a constant temperature bath 102 equipped with a Peltier element or the like for temperature control, a gel pump unit 103 for supplying an electrophoresis medium to the capillaries in the capillary array, a detection unit 104, and an autosampler 105. A capillary array can be disposed in the space inside the constant temperature bath. The autosampler 105 is adapted such that a sample plate assembly and a buffer tank or the like, which will be described later, can be mounted on trays.

Figure 2:
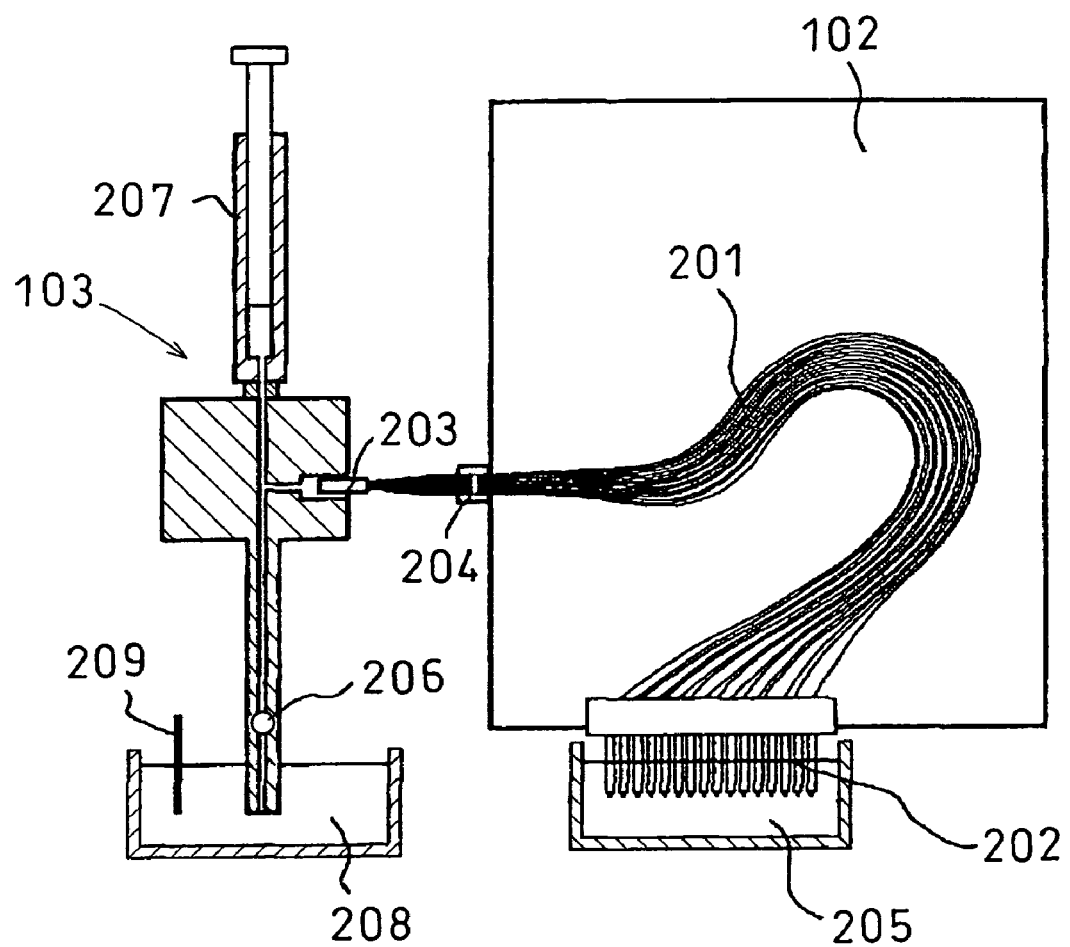

FIG. 2 illustrates the relationships among a capillary array unit 201, the constant temperature bath 102, the gel pump unit 103, and the like. One end of the capillary array unit 201 comprises sample injection ends that are inserted into hollow electrodes 202 made of hollow stainless steel pipes. Capillaries protrude slightly beyond the tips of the hollow electrodes 202. The gap between each capillary and each hollow electrode 202 is sealed with glue so that no carryover of the sample or the like is caused. When a DNA sample is injected into the capillaries, the sample injection ends of the capillaries are submerged in a solution containing the DNA sample. When the injected sample is electrophoresed, the sample injection end is submerged in a buffer solution 205 and a voltage is applied between both ends of the capillaries. In FIG. 2, the sample injection end is submerged in the buffer solution 205, and the DNA sample is not shown.

On the other end of the capillary array unit 201 is formed a capillary head 203 which is adapted to be connected to the gel pump unit 103 for the injection of a gel as a migration medium into the capillary array unit 201. When the gel, or the migration medium inside the capillaries, is charged into the capillaries, a valve 206 is closed and a syringe 207 is pressed down, such that the gel inside the syringe 207 can be injected into the capillary array unit 201. During electrophoresis, the valve 206 is opened, and a voltage is applied between the electrodes 202 immersed in the buffer 205 and a ground electrode 209 immersed in a buffer 208. The capillary array unit 201 is almost entirely housed inside the constant temperature bath 102, which is of gas circulation type, except for its both end portions, so that the temperature of the unit can be maintained at a certain level. A detector unit 204 is disposed outside the constant temperature bath 102 for detecting fluorescence emitted by the fluorescence-labeled sample separated by electrophoresis in the capillaries.

Figure 3:
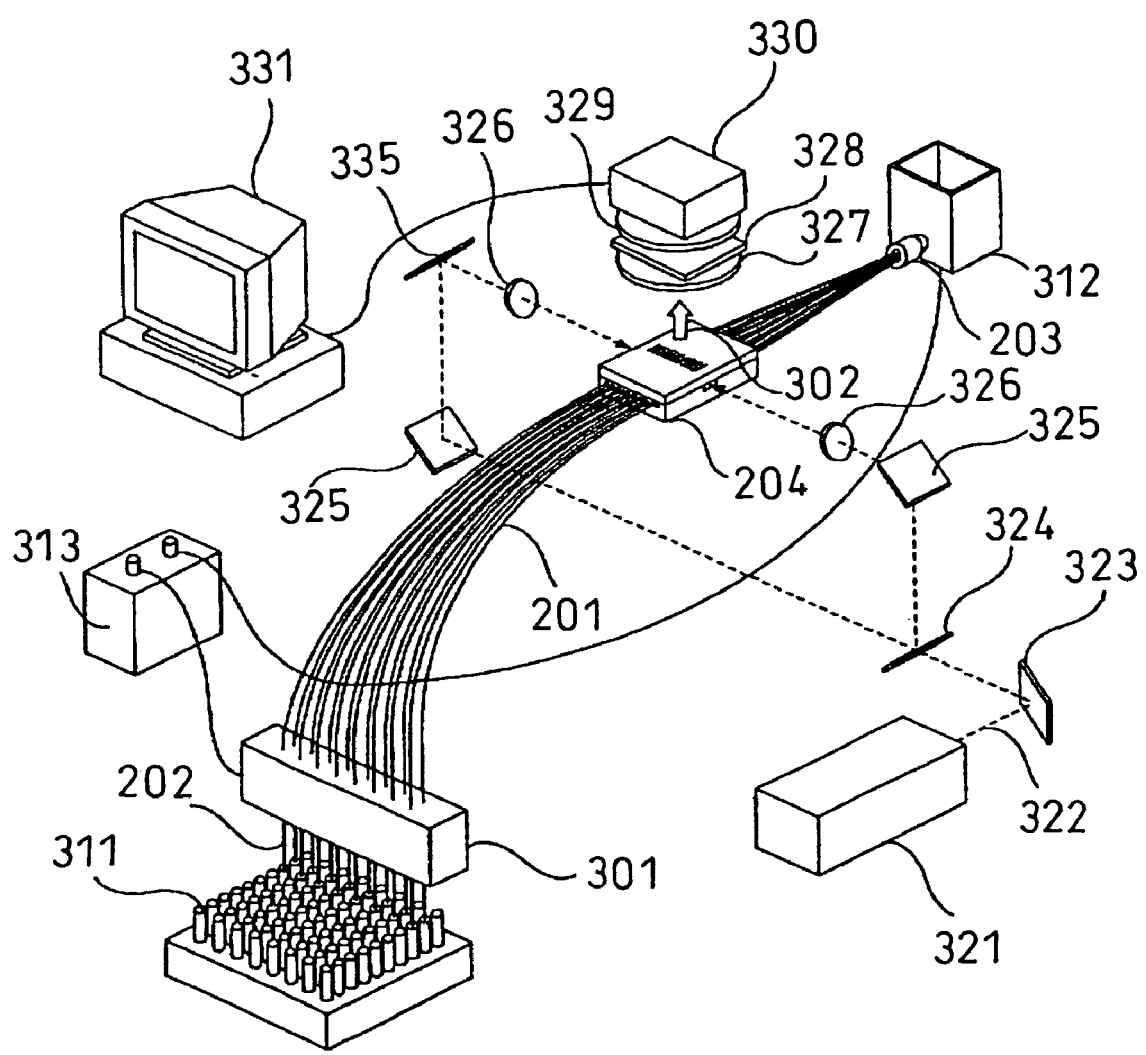

FIG. 3 schematically shows an electrophoresis system. Each capillary in the capillary array unit 201 is made of a quartz pipe with an external diameter of 0.1 to 0.7 mm and an inner diameter of 0.02 to 0.5 mm, and is coated with polyimide resin on the outside. A plurality (usually from several to several tens) of such capillaries are arranged to form the capillary array unit 201. The capillary array unit 201 includes a load header 301 for loading of samples into the capillaries by electrophoresis from a sample container containing fluorescence-labeled DNA samples or the like. The unit also includes the detector unit (window unit) 204 in which the capillaries are arranged and fixed in order of sample numbers on the load header 301, and the capillary head 203 in which the plurality of capillaries are bundled and glued together. The load header 301 is provided with an electrode for applying a migration voltage to the capillaries. The electrode is connected to the hollow electrodes 202 in which the sample injection end of each capillary is inserted. The detector (window unit) 204 is provided with an opening via which the capillaries arranged and retained is irradiated with light, and another opening via which to pick up light emission 302 from the capillaries.

The hollow electrodes 202 protruding from the load header 301 and the sample injection ends of the capillaries of the capillary array unit 201 are submerged in a sample container 311 containing the fluorescence-labeled DNA samples. The capillary head 203 on the other end is attached to a buffer container 312 containing a buffer. Between the buffer container 312 and the load header 301 is applied a high voltage of about 15 kV from a high-voltage power supply 313, whereby the samples in the sample container 311 are injected via the sample injection ends of the capillaries by electric field injection. Thereafter, the sample container 311 is removed, and the sample injection ends of the capillary array unit 201 are immersed in the buffer, as shown in FIG. 2. A voltage is then applied between both ends of the capillaries to carry out electrophoresis of the samples.

The electrophoresed samples are detected by the detector unit (window unit) 204. Laser light 322 is emitted by a laser light source 321. The laser light is reflected by a reflecting mirror 323, divided into two portions by a beam splitter 324, reflected by reflecting mirrors 325, and then condensed by condenser lenses 326 such that the capillary array unit 201 is irradiated with the light from a direction parallel to the plane in which the capillaries are arranged. The fluorescence-labeled samples that have electrophoretically migrated in the gel filled in the capillaries are excited by the irradiation of laser light 322, thereby emitting fluorescence 302. The fluorescence 302 propagating in a direction substantially perpendicular to the plane in which the capillaries are arranged is rendered into parallel light by a first lens 327, the image is divided by an optical filter and an image splitting prism 328, and then the image is focused on a CCD camera 330 by a second lens 329. The measurement data detected by the CCD camera 330 is processed by a processing and computing unit 331 to analyze the base sequence or base length of the DNA samples. While in the figure the laser light 322 irradiates the detector unit 204 from either side thereof, the irradiation may occur on one side thereof.

The DNA sample or buffer solutions are transported by the autosampler 105 that is movable in X, Y and Z directions, such that the sample introduction end of each capillary in the capillary array unit 201 is inserted into a desired container. The present invention provides a means for fixing the containers containing the DNA sample or buffers, for example, on the autosampler 105. Specific examples will be described in detail below.

In order to reduce the load on the person who does the analysis, the samples to be analyzed are analyzed on a commercially available microtiter plate. As the microtiter plate cannot be set on a tray of the autosampler as is, it is set on the tray as part of a four-layer structure sample plate assembly consisting of a plate adapter, the plate, a septum, and a septum holder. There are various microtiter plates available with corresponding adapters, so that any type of plate can be mounted on the autosampler. Two types of microtiter plates are available, one with 8×12=96 wells and the other with 16×24=384 wells. The electrophoretic device of the invention can accommodate two sets of the aforementioned sample plate assemblies simultaneously, so that a maximum of 384×2=768 samples can be continuously analyzed.

Figure 4:
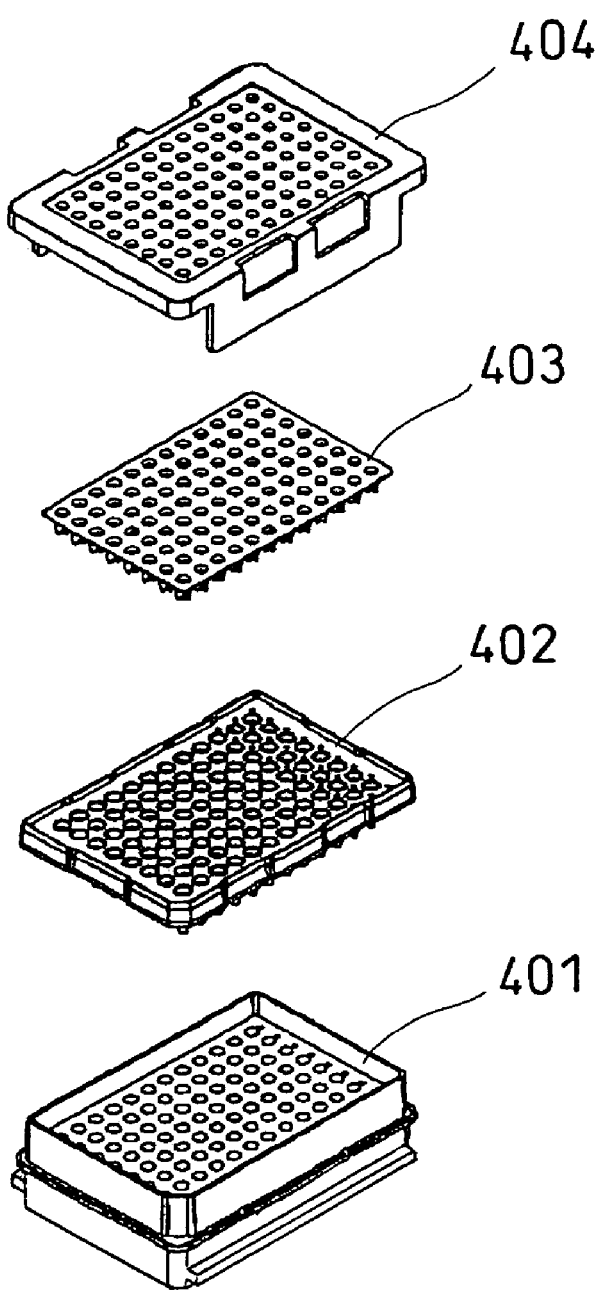
FIG. 4 is an exploded view of a sample plate assembly.
Figure 5:
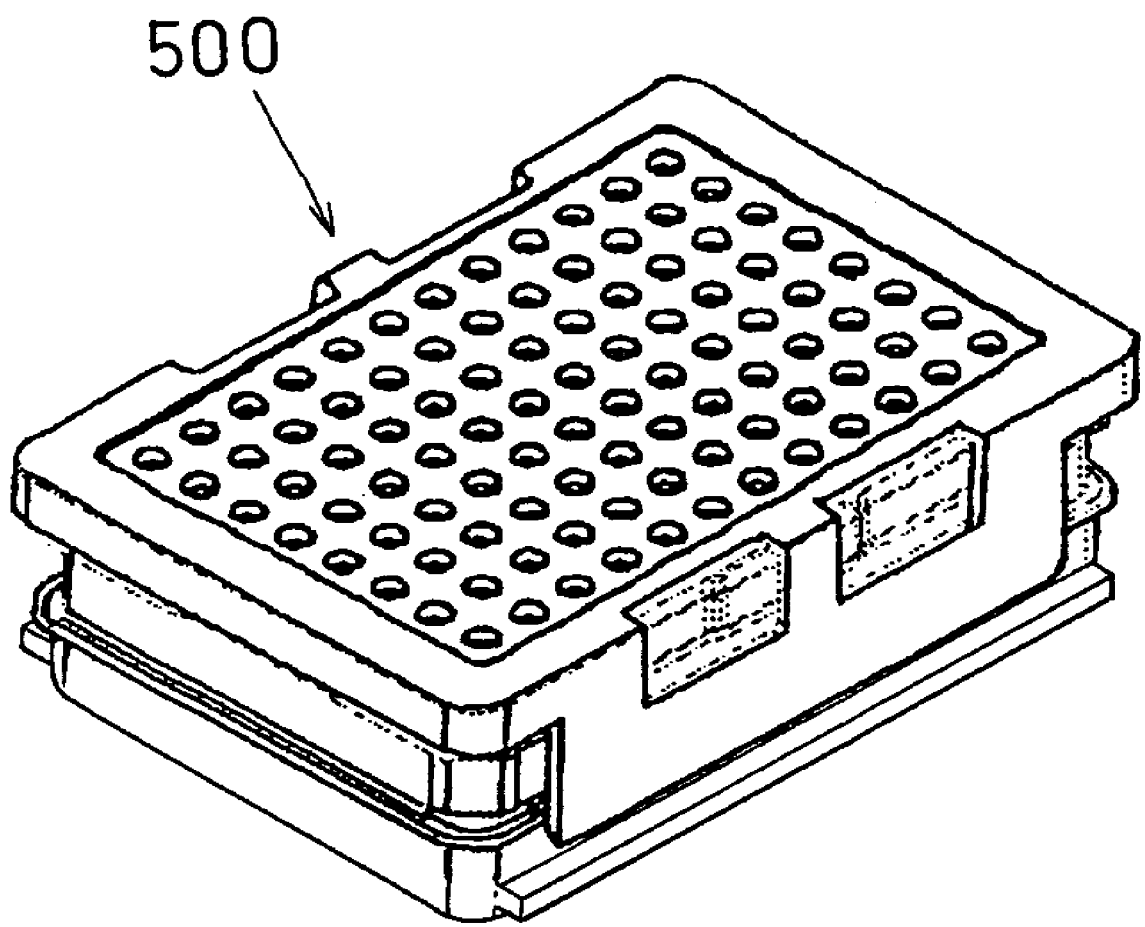
FIG. 5 is a perspective view of the sample plate assembly.
Figure 6:
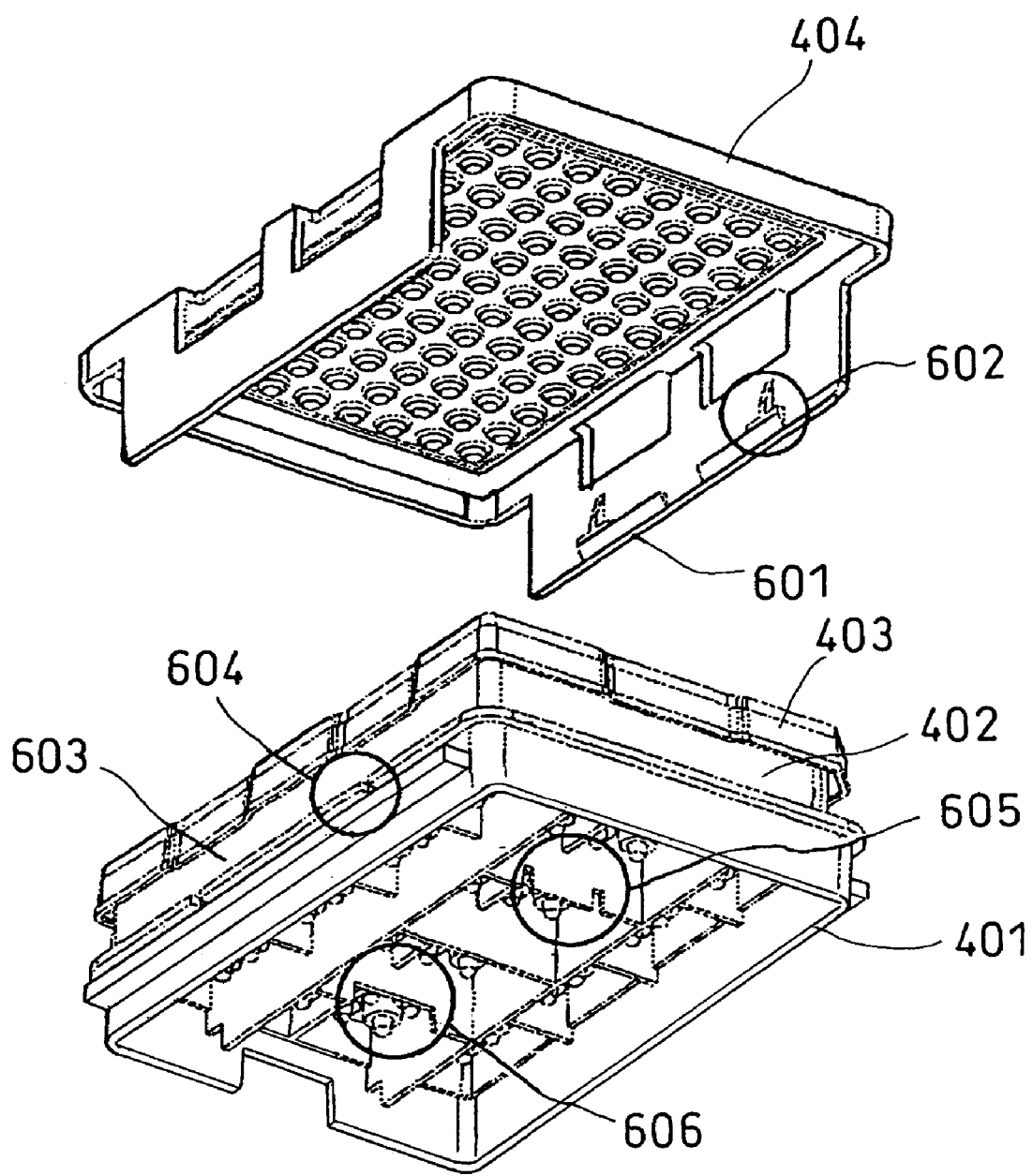
FIG. 6 is a bottom view of the sample plate assembly.

FIGS. 4 to 6 show a sample plate assembly with a 96-well microtiter plate. FIG. 4 shows an exploded view, FIG. 5 shows a perspective view of the sample plate assembly as assembled, and FIG. 6 shows a bottom view.

The sample plate assembly is made up of a plate adapter 401, a microtiter plate 402, a septum 403, and a septum holder 404. The plate adapter 401 is the mount with which the microtiter plate 402 can be set on the tray of the autosampler 105. The septum 403 is made of silicon rubber and is formed with projections whose tips are adapted to enter into the individual wells on the microtiter plate 402. These tips are provided with cuts for the passage of the tips of the capillaries. The septum 403 has the function of preventing sample evaporation and that of wiping off samples or the like that have attached to the capillary tips. The septum holder 404 is a component for securing the microtiter plate 402 and the septum 403 to the adapter 401.

FIG. 5 shows a sample plate assembly 500 assembled from the septum holder 404, septum 403, microtiter plate 402 and plate adapter 401. FIG. 6 shows the sample plate assembly from which the septum holder 404 has been detached. The septum holder 404 also has the function of correcting the shape of the microtiter plate 402 and securing it onto the adapter 401 correctly, as the microtiter plate 402 is used in a thermal process called PCR (Polymerase Chain Reaction), which is a pre-processing for the samples, and could be deformed under certain conditions. At the bottom of the plate adapter 401 is provided a light-shielding plate 605 or a notch 606 for identifying the type of the plate adapter with a photo interrupter. The plate adapter 401 also has guides 715 and 716 formed at different heights on either lengthwise side thereof.

The septum holder 404 has two nails 601 on either side, as shown in FIG. 6, which are adapted to be hooked with a flange 603 on the adapter 401, so that the holder can be simply mounted on the adapter 401 without bothering the analyzer. As a result, the septum holder 404 could possibly be displaced along the length of the plate adapter 401 when they are fitted together. If the septum holder 404 is thus incorrectly secured to the plate adapter 401, the openings of the septum holder 404 through which the capillaries are passed would not coincide with the wells in the microtiter plate 402, which would damage the capillaries. To prevent this, projections 602 are provided at the nails 601 at four locations on the septum holder 404, whereby the nails 601 cannot engage with the flange 603 unless the projections 602 are matched up with guides 604 on the adapter, thus limiting the manner in which the septum holder 404 can be mounted on the plate adapter 401. Thus, the analyzer can mount the septum holder 404 on the plate adapter 401 without paying any particular attention, and the problem of mounting it at a wrong position can simultaneously be eliminated.

The autosampler of the invention can accommodate different plates (heights) by means of the adapter. Several types of microtiter plates with 96 wells are commercially available that can be used with the electrophoretic device of the invention, with different shapes, sizes and depths of the wells depending on the manufacturers. If the minimum sample amount for the electrophoretic device of the invention is set to be at 10 µl, the height from the bottom of the well to the sample level can be about 2.5 mm, for example, in the case of some commercially available 96-well microtiter plates. Thus, the capillaries must be inserted to the depth of about 1 mm from the bottom of the well if the samples are to be introduced into the capillaries in a reliable manner. However, the height of the bottom of the well greatly varies depending on each microtiter plate, so that, if no distinctions are made between the individual microtiter plates, the tip of the capillaries could hit the bottom and be damaged, or it would not reach the samples and thus fail to have the samples introduced into the capillaries.

Thus, in order to correct the height of the bottom of the well or the position of the central axis among the microtiter plates from various manufacturers, plate adapters are prepared that are adapted to individual microtiter plates. By using them in various combinations, any microtiter plate with 96 wells can be positioned on the tray on the autosampler at the same location in terms of the central axis of the well and the height of the bottom. Accordingly, it is only necessary for the autosampler to recognize the number of the wells (96 or 384) on the sample plate assembly mounted thereon and select the control method accordingly. In this way, the autosampler can be moved by the same control method at all times regardless of the type of the 96-well microtiter plate mounted.

While it is not easy to distinguish the 96-well microtiter plates from the various manufacturers at a glance, the individual plate adapter is provided with features such that it will not be attached to a wrong plate adapter or attached in a wrong direction. For example, in the case of the microtiter plate 402 shown in FIG. 4, one of the four corners is cut off. The direction or size of the cutoff varies for individual microtiter plates, and the plate adapter 401 is also shaped to correspond to each cutoff. Thus, the chances of attaching the microtiter plate to a wrong plate adapter or in a wrong direction can be eliminated.

The autosampler of the invention can deal with 96/384 with the same structure. Two sets of the plate adapter for 96-well microtiter plates and the plate adapter for 384-well microtiter plates can be mounted on the tray on the autosampler in any combination selected by the user in light of the purpose of analysis.

Figure 7:
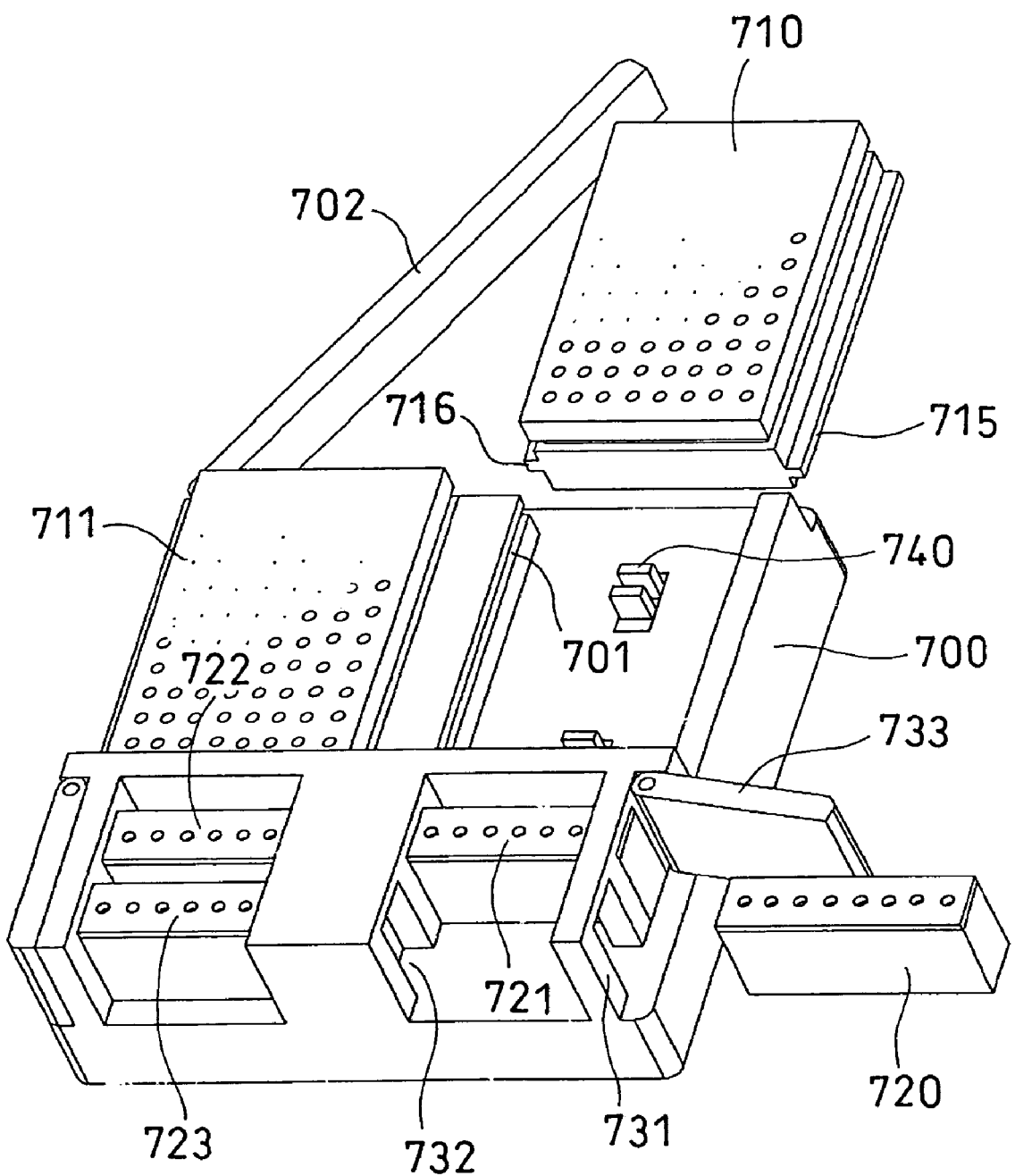
FIG. 7 shows an example of a tray of an autosampler according to the invention.

FIG. 7 shows an example of the tray of the autosampler of the invention. A tray 700 in the illustrated example is capable of mounting two sets of sample plate assemblies and four sets of tanks for storing buffers or water, for example. As many of these assemblies or tanks as necessary for electrophoresis may be mounted.

On either side of the location for the mounting of the sample plate assembly is provided a horizontal guide groove 701. Sample plate assemblies 710 and 711 (which are drawn in a simplified form in FIG. 7 but which actually have a multilayer structure, as shown in FIG. 5) are set on the tray 13 in the following manner. They are slid horizontally from the outside of the tray 13 such that guides 715 and 716 horizontally provided on either side of each assembly are engaged with the guide grooves 701 on the tray 700. Thus the sample plate assemblies 710 and 711 can be secured on the tray 700 in vertical (Z) direction. The sample plate assemblies 710 and 711 are fixed in the direction along the guide grooves 701 of the tray 700 by closing a cover 702 provided on the tray 700 once the assemblies are inserted to the end of the grooves 701. The cover 702 is secured to the side of the tray 700 by means of a nail, screw, or magnet, for example, provided at the tip of the cover.

At the location of the tray 700 where tanks are disposed is provided a gate-shaped frame 731 and a recessed portion 732. Tanks 720 to 723 are mounted on the tray 700 by passing through the gate-shaped frame 731 and then having the end of each tank inserted into the recessed portion 732. Thereafter, a cover 734 is closed so as to restrict the movement of the tanks out of the 731. Thus, the tanks 720 to 723 are secured in place in vertical and horizontal directions.

Thus, the sample plate assemblies 710 and 711 and the tanks 720 to 723 are secured in place on the tray 700 in all of the X, Y and Z directions, thereby eliminating the problems of the microtiter plates, the tanks, or the septa thereon being lifted when the sample introduction end of the capillary array unit 201 is moved up or down in the microtiter plates or tanks in response to the up/down movement of the autosampler. Accordingly, there is no need to provide a separate mechanism for pushing the sample plate assemblies or the tanks against the tray, such as the stripper plate.

On the tray 700 are mounted two photo interrupters 740 for each location where the sample plate assembly is mounted, for a total of four photo interrupters. These photo interrupters are used for automatically identifying microtiter plates with different numbers of wells. The present embodiment is adapted for two kinds of microtiter plates with 96 and 384 wells, and which microtiter plates are mounted is automatically identified.

Different types of adapter 401 are prepared for the two types of microtiter plates, and each adapter is provided with a light-shielding plate at a different location. As the adapter is set on the tray 700, the light-shielding plate blocks the light emitted by one of the two photo interrupters 740 on the tray 700. Further, the guide grooves 701 on the sides of the tray 700 are provided at different heights so as to fix the direction in which the adapter is mounted. Similarly, the guides 715 and 716 on the sides of the adapter 401 are provided at different heights to be matched with the guide grooves on the tray 700. Therefore, the two types of adapters can be set on the tray 700 only in one direction, thereby making sure that the adapters will not be misidentified by the photo interrupters 740. Based on signals from the photo interrupters, which type of microtiter plate is mounted can be automatically identified, whereby the autosampler can be operated while switching the distance of its travel in accordance with the pitch of wells.

The arrangement of the sample plate assemblies and tanks, the direction in which they are slid, the direction of opening or closing of the covers, and so on, are not limited to those shown in FIG. 7, and they may be modified in accordance with the arrangement of the autosampler in the electrophoretic device or the size of the space that is provided in areas surrounding the tray.

Figure 8:
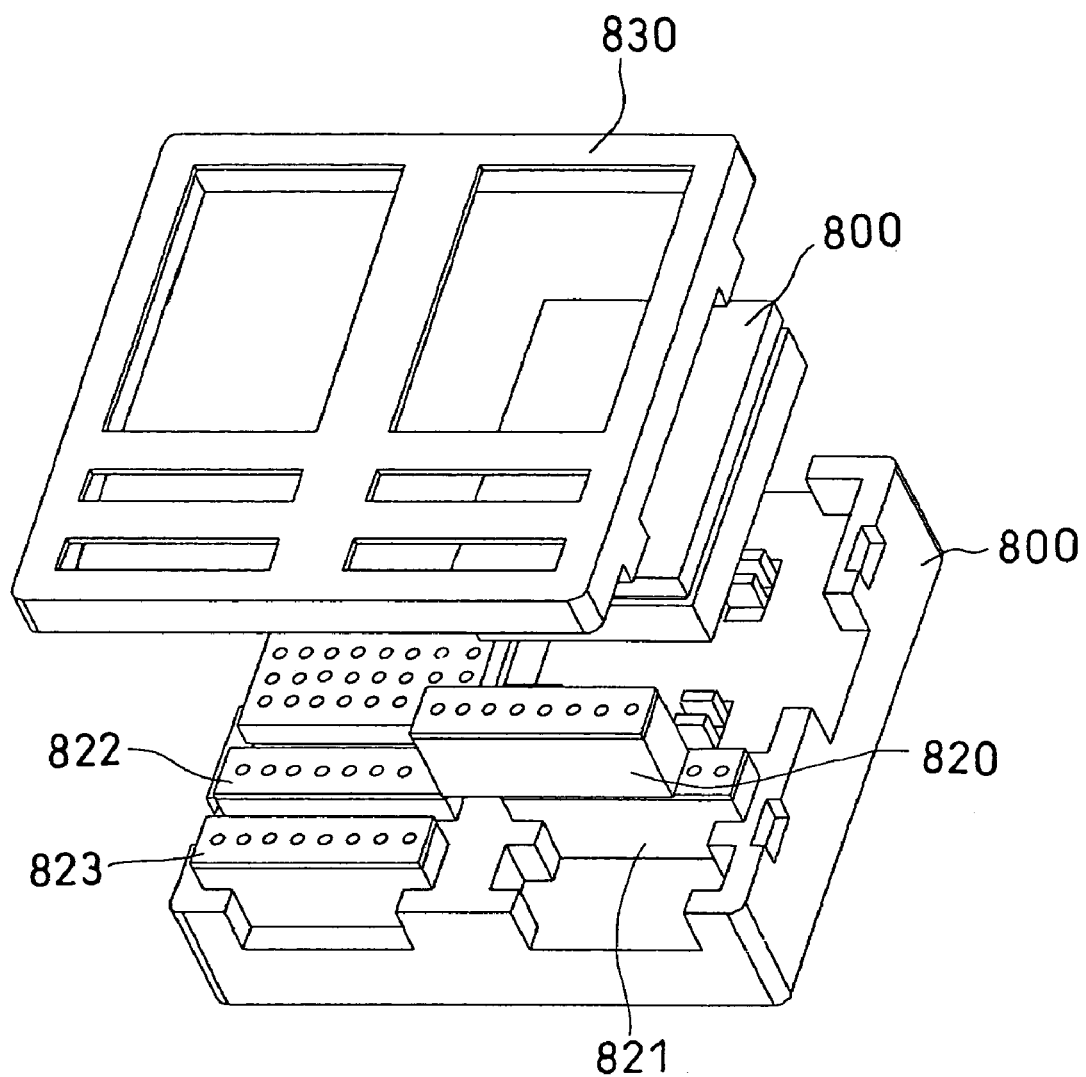
FIG. 8 shows another example of the tray of the autosampler according to the invention.

FIG. 8 shows another example of the tray for the autosampler in accordance with the present invention. A tray 800 in this example is capable of mounting two sets of sample plate assemblies 810 and 811 and four sets of tanks 820 to 823, as the tray 700 shown in FIG. 7 is. The tray 800 differs from the tray 700 in the manner in which the sample plate assemblies and tanks are mounted and secured. Other points are similar to those of the example of FIG. 7 and are therefore not described.

The sample plate assemblies 800 and 801 and the tanks 820 to 823 are set on the tray 800 from above along guides thereof. In this case, the vertical walls on the tray 800 surrounding the locations where the sample plate assemblies and the tanks are to be mounted function as the guides. No special guides are required on the sides of the sample plate assemblies 800 and 801, in contrast to the example of FIG. 7. Once set on the tray 800 from above, the assemblies 800 and 801 and the tanks 820 to 823 are fixed in place in X and Y directions. A clip 830 is then attached from above the tray 800 in such a manner as to cover the sample plate assemblies 800 and 801 and the tanks 820 to 823, thereby securing the assemblies and tanks in Z direction.

In the example shown in FIG. 8, the sample plate assemblies and tanks are all fastened with a single clip 830. However, the clip may be divided into two portions, one for the sample plate assemblies and the other for the tanks, for example. Further, while in the example of FIG. 8 the clip 830 is an independent part from the tray 800, an integral, openable clip/tray cover may be employed. Such an integral cover may of course be further divided into multiple covers.

INDUSTRIAL APPLICABILITY

In accordance with the invention, sample containers, buffer containers or the like can be easily mounted on a tray of an autosampler and fixed thereon in X, Y and Z directions. As the invention does not require the use of the conventional stripper plate, the structure of the device can be simplified, and the length of the capillary array that is exposed outside a constant temperature bath can be minimized, thus enhancing analysis accuracy.

The invention claimed is:

1. A capillary array electrophoretic device comprising:
a capillary array made up of a plurality of capillaries with their sample injection ends arranged in order;
a constant temperature bath for storing the capillary array with the sample injection ends disposed downward and exposed; and
an autosampler comprising a tray on which a plurality of sample containers and buffer containers can be mounted, the autosampler being adapted to move vertically and horizontally such that, when moved upward, the sample injection ends exposed from the constant temperature bath can be immersed in a sample in the sample containers or a buffer in the buffer containers, wherein the plurality of sample containers and buffer containers are fixed on the tray in the autosampler, wherein the sample containers are fixed in the vertical direction by means of a horizontal guide groove provided in the tray while they are fixed in a direction along the guide groove as a cover fixed on one end thereof to the tray is closed.

2. The capillary array electrophoretic device according to claim 1, wherein the autosampler comprises a guide and a stopper for retaining a sample plate assembly and fixing it three dimensionally on the tray, the sample plate assembly including a microtiter plate for storing samples and an adapter on which the microtiter plate is to be mounted.

3. The capillary array electrophoretic device according to claim 2, wherein different types of the adapter are prepared for different microtiter plates.

4. The capillary array electrophoretic device according to claim 2, wherein the tray includes a sensor for detecting the shape of a bottom portion of the adapter in order to identify the number of wells of the microtiter plate mounted on the adapter.

5. The capillary array electrophoretic device according to claim 2, wherein the tray includes a sensor for detecting the shape of a bottom portion of the adapter in order to identify the type of the microtiter plate mounted on the adapter.

6. The capillary array electrophoretic device according to claim 2, wherein the sample plate assembly comprises a septum holder that can secure the microtiter plate to the adapter.

7. An autosampler provided in a capillary array electrophoretic device in which a capillary array is mounted with a sample injection end exposed outside a constant temperature bath, the autosampler comprising a tray on which a plurality of sample containers and buffer containers can be mounted, the autosampler being adapted to move vertically and horizontally such that, when moved upward, the sample injection end exposed from the constant temperature bath can be immersed in a sample in the sample containers or a buffer in the buffer containers, wherein
the plurality of sample containers and buffer containers are fixed on the tray, wherein the sample containers are fixed in the vertical direction by means of a horizontal guide groove provided in the tray while they are fixed in a direction along the guide groove as a cover fixed on one end thereof to the tray is closed.

8. The autosampler according to claim 7, wherein the left and right guide grooves have different heights.

9. The autosampler according to claim 7, further comprising a guide and a stopper for retaining a sample plate assembly and fixing it three dimensionally on the tray, the sample plate assembly including a microtiter plate for storing samples and an adapter on which the microtiter plate is mounted.

10. The autosampler according to claim 9, wherein different types of the adapter are prepared for different microtiter plates.

11. The autosampler according to claim 9, wherein the tray includes a sensor for detecting the shape of a bottom portion of the adapter in order to identify the number of wells of the microtiter plate mounted on the adapter.

12. The autosampler according to claim 9, wherein the tray includes a sensor for detecting the shape of a bottom portion of the adapter in order to identify the type of the microtiter plate mounted on the adapter.

13. The autosampler according to claim 9, wherein the sample plate assembly comprises a septum holder that can secure the microtiter plate to the adapter.

* * * * *